United States Patent
Chandra et al.

(10) Patent No.: US 9,174,904 B1
(45) Date of Patent: Nov. 3, 2015

(54) SYNTHESIS OF 2,2-BIS(3-PHENYL-4-HYDROXYPHENYL) PROPANE (PHP)

(71) Applicant: SABIC Global Technologies B.V., Bergen op Zoom (NL)

(72) Inventors: Girish Chandra, Bangalore (IN); Meerakani Mohamed Ali Sait, Bangalore (IN); Akhilesh Tanwar, Bangalore (IN); Sharankumar Shetty, Bangalore (IN)

(73) Assignee: SABIC Global Technologies B.V., Bergen op Zoom (NL)

( * ) Notice: Subject to any disclaimer, the term of this patent is extended or adjusted under 35 U.S.C. 154(b) by 0 days.

(21) Appl. No.: 14/331,583

(22) Filed: Jul. 15, 2014

(51) Int. Cl.
| | |
|---|---|
| *C08G 65/38* | (2006.01) |
| *C07C 37/20* | (2006.01) |
| *C07C 39/15* | (2006.01) |
| *C08G 63/02* | (2006.01) |

(52) U.S. Cl.
CPC .................. *C07C 37/20* (2013.01); *C07C 39/15* (2013.01)

(58) Field of Classification Search
CPC ........................................................ C08G 65/38
USPC ........................................................... 528/219
See application file for complete search history.

(56) References Cited

U.S. PATENT DOCUMENTS

| | | | |
|---|---|---|---|
| 3,635,895 A | 1/1972 | Morton | |
| 4,001,184 A | 1/1977 | Scott | |
| 4,996,373 A * | 2/1991 | Bottenbruch et al. | 568/727 |
| 7,786,246 B2 | 8/2010 | Jansen et al. | |

OTHER PUBLICATIONS

Si, Chunyan; Lin, Ling; Zeng, Chongyu; Synthesis and characterization of bis-OPP-A School of Chemistry and Chemical Engineering, Nanjing University of Technology, Nanjing, 210009, Peoples Rep. China, Huagong Shikan (2007), vol. 21(4), 1-4.*
U.S. Appl. No. 14/284,040, filed May 21, 2014, Shetty et al.

* cited by examiner

*Primary Examiner* — Terressa Boykin
(74) *Attorney, Agent, or Firm* — Baker Hostetler LLP

(57) ABSTRACT

Disclosed herein are ortho aryl substituted bisphenol monomers that exhibit a lower binding energy to estradiol related receptors. The monomers are provided by the condensation of a ketone and phenol in the presence of an acid catalyst.

14 Claims, No Drawings

SYNTHESIS OF 2,2-BIS(3-PHENYL-4-HYDROXYPHENYL) PROPANE (PHP)

BACKGROUND

Bisphenol based monomers are widely used precursors in the production of polycarbonate materials. Development of alternatives to existing polycarbonates, polyesters and polyestercarbonates that maintain properties (high transparency and good melt stability) of the corresponding polymers are of great interest in the plastics industry and for the manufacturing industry. To achieve this, a suitable monomer for polymerization reactions is necessary to produce a polymer with the necessary properties.

Further, monomers or oligomers used in making the polycarbonate materials may not proceed to completion in some instances, thus leading to the presence of unreacted residual monomers or oligomers in the polymeric material. Additionally, when subjected to certain conditions, the polymeric materials can undergo degradation reactions, such as hydrolytic or thermolytic degradation, resulting in the formation of hydrolysis and/or thermolysis degradants or reaction products. In some aspects, the resulting degradants can correspond chemically to the monomeric starting materials initially used to manufacture polymeric materials. The presence of residual monomers, either as residues of polymerization or through degradation by thermal or hydrolytic means, is an area of growing regulatory concern.

This concern has led to extensive research to find suitable alternative monomers for polycarbonate materials whose residual monomers or degradation products exhibit desirable characteristics. Desirable characteristics of such degradants include, among other, extremely low, or even no estradiol related receptor (ERR) binding activity.

Accordingly, there is a need for polymeric materials which, if having or generating residual monomers, comprise such monomers that have very low, or nondetectable, biological activity, for instance having extremely low or no binding activity compared to estradiol in the estradiol related receptors (ERR) e.g., ERR-α and/or ERR-β.

SUMMARY

The present disclosure relates to a synthesis of 2,2-bis(3-phenyl-4-hydroxyphenyl) propane (PHP) monomer as a suitable monomer for polymerization reactions to ensure low binding to the estradiol related receptors compared to estradiol. As an example, the PHP monomer of the present disclosure has bulkier group in ortho position to hydroxyl group, which can have relatively low binding to the estradiol related receptors (ERR). The method for making the PHP monomers can comprise reacting acetone and 2-phenylphenol in the presence of an acid. The monomers can be used in the production of polymer compositions which can be used in the manufacture of articles requiring materials with low cost, low color, high transparency, and good melt stability.

In one aspect, the disclosure relates to the efficient synthesis of an ortho aryl substituted bisphenol polymer. In further aspects, the ortho aryl substituted bisphenol polymer is PHP.

In further aspects, the disclosure relates to polymers comprising the disclosed monomers.

In various further aspects, the disclosure relates to articles comprising the disclosed monomer.

In a further aspect, the disclosure relates to methods of making the disclosed monomers.

While aspects of the present disclosure can be described and claimed in a particular statutory class, such as the system statutory class, this is for convenience only and one of skill in the art will understand that each aspect of the present disclosure can be described and claimed in any statutory class. Unless otherwise expressly stated, it is in no way intended that any method or aspect set forth herein be construed as requiring that its steps be performed in a specific order. Accordingly, where a method claim does not specifically state in the claims or descriptions that the steps are to be limited to a specific order, it is no way intended that an order be inferred, in any respect. This holds for any possible non-express basis for interpretation, including matters of logic with respect to arrangement of steps or operational flow, plain meaning derived from grammatical organization or punctuation, or the number or type of aspects described in the specification.

Additional aspects of the disclosure will be set forth in part in the description which follows, and in part will be obvious from the description, or can be learned by practice of the disclosure. The advantages of the disclosure will be realized and attained by means of the elements and combinations particularly pointed out in the appended claims. It is to be understood that both the foregoing general description and the following detailed description are exemplary and explanatory only and are not restrictive of the disclosure, as claimed.

DETAILED DESCRIPTION

The present disclosure can be understood more readily by reference to the following detailed description of the disclosure and the Examples included therein.

Before the present compounds, compositions, articles, systems, devices, and/or methods are disclosed and described, it is to be understood that they are not limited to specific synthetic methods unless otherwise specified, or to particular reagents unless otherwise specified, as such can, of course, vary. It is also to be understood that the terminology used herein is for the purpose of describing particular aspects only and is not intended to be limiting. Although any methods and materials similar or equivalent to those described herein can be used in the practice or testing of the present disclosure, example methods and materials are now described.

Moreover, it is to be understood that unless otherwise expressly stated, it is in no way intended that any method set forth herein be construed as requiring that its steps be performed in a specific order. Accordingly, where a method claim does not actually recite an order to be followed by its steps or it is not otherwise specifically stated in the claims or descriptions that the steps are to be limited to a specific order, it is no way intended that an order be inferred, in any respect. This holds for any possible non-express basis for interpretation, including: matters of logic with respect to arrangement of steps or operational flow; plain meaning derived from grammatical organization or punctuation; and the number or type of embodiments described in the specification.

All publications mentioned herein are incorporated herein by reference to disclose and describe the methods and/or materials in connection with which the publications are cited.

A. DEFINITIONS

It is also to be understood that the terminology used herein is for the purpose of describing particular aspects only and is not intended to be limiting. As used in the specification and in the claims, the term "comprising" can include the embodiments "consisting of" and "consisting essentially of" Unless defined otherwise, all technical and scientific terms used herein have the same meaning as commonly understood by one of ordinary skill in the art to which this disclosure belongs. In this specification and in the claims which follow, reference will be made to a number of terms which shall be defined herein.

As used in the specification and the appended claims, the singular forms "a," "an" and "the" include plural referents unless the context clearly dictates otherwise. Thus, for example, reference to "a polycarbonate poly" includes mixtures of two or more polycarbonate polymers.

As used herein, the term "combination" is inclusive of blends, mixtures, alloys, reaction products, and the like.

Ranges can be expressed herein as from one particular value, and/or to another particular value. When such a range is expressed, another aspect includes from the one particular value and/or to the other particular value. Similarly, when values are expressed as approximations, by use of the antecedent 'about,' it will be understood that the particular value forms another aspect. It will be further understood that the endpoints of each of the ranges are significant both in relation to the other endpoint, and independently of the other endpoint. It is also understood that there are a number of values disclosed herein, and that each value is also herein disclosed as "about" that particular value in addition to the value itself. For example, if the value "10" is disclosed, then "about 10" is also disclosed. It is also understood that each unit between two particular units are also disclosed. For example, if 10 and 15 are disclosed, then 11, 12, 13, and 14 are also disclosed.

As used herein, the terms "about" and "at or about" mean that the amount or value in question can be the value designated some other value approximately or about the same. It is generally understood, as used herein, that it is the nominal value indicated ±10% variation unless otherwise indicated or inferred. The term is intended to convey that similar values promote equivalent results or effects recited in the claims. That is, it is understood that amounts, sizes, formulations, parameters, and other quantities and characteristics are not and need not be exact, but can be approximate and/or larger or smaller, as desired, reflecting tolerances, conversion factors, rounding off, measurement error and the like, and other factors known to those of skill in the art. In general, an amount, size, formulation, parameter or other quantity or characteristic is "about" or "approximate" whether or not expressly stated to be such. It is understood that where "about" is used before a quantitative value, the parameter also includes the specific quantitative value itself, unless specifically stated otherwise.

As used herein, the terms "optional" or "optionally" means that the subsequently described event or circumstance can or cannot occur, and that the description includes instances where said event or circumstance occurs and instances where it does not. For example, the phrase "optionally substituted alkyl" means that the alkyl group can or cannot be substituted and that the description includes both substituted and unsubstituted alkyl groups.

As used herein, the term "effective amount" refers to an amount that is sufficient to achieve the desired modification of a physical property of the composition or material. For example, an "effective amount" of a thermally conductive filler refers to an amount that is sufficient to achieve the desired improvement in the property modulated by the formulation component, e.g. achieving the desired level of thermal conductivity. The specific level in terms of wt % in a composition required as an effective amount will depend upon a variety of factors including the amount and type of polycarbonate, amount and type of polycarbonate, amount and type of thermally conductive filler, and end use of the article made using the composition.

Disclosed are the components to be used to prepare the compositions of the disclosure as well as the compositions themselves to be used within the methods disclosed herein. These and other materials are disclosed herein, and it is understood that when combinations, subsets, interactions, groups, etc. of these materials are disclosed that while specific reference of each various individual and collective combinations and permutation of these compounds cannot be explicitly disclosed, each is specifically contemplated and described herein. For example, if a particular compound is disclosed and discussed and a number of modifications that can be made to a number of molecules including the compounds are discussed, specifically contemplated is each and every combination and permutation of the compound and the modifications that are possible unless specifically indicated to the contrary. Thus, if a class of molecules A, B, and C are disclosed as well as a class of molecules D, E, and F and an example of a combination molecule, A-D is disclosed, then even if each is not individually recited each is individually and collectively contemplated meaning combinations, A-E, A-F, B-D, B-E, B-F, C-D, C-E, and C-F are considered disclosed. Likewise, any subset or combination of these is also disclosed. Thus, for example, the sub-group of A-E, B-F, and C-E would be considered disclosed. This concept applies to all aspects of this application including, but not limited to, steps in methods of making and using the compositions of the disclosure. Thus, if there are a variety of additional steps that can be performed it is understood that each of these additional steps can be performed with any specific aspect or combination of aspects of the methods of the disclosure.

References in the specification and concluding claims to parts by weight, of a particular element or component in a composition or article, denotes the weight relationship between the element or component and any other elements or components in the composition or article for which a part by weight is expressed. Thus, in a compound containing 2 parts by weight of component X and 5 parts by weight component Y, X and Y are present at a weight ratio of 2:5, and are present in such ratio regardless of whether additional components are contained in the compound.

As used herein the terms "weight percent," "wt %," and "wt. %," which can be used interchangeably, indicate the percent by weight of a given component based on the total weight of the composition, unless otherwise specified. That is, unless otherwise specified, all wt % values are based on the total weight of the composition. It should be understood that the sum of wt % values for all components in a disclosed composition or formulation are equal to 100.

Compounds are described using standard nomenclature. For example, any position not substituted by any indicated group is understood to have its valence filled by a bond as indicated, or a hydrogen atom. A dash ("—") that is not between two letters or symbols is used to indicate a point of attachment for a substituent. For example, —CHO is attached through carbon of the carbonyl group. Unless defined otherwise, technical and scientific terms used herein have the same meaning as is commonly understood by one of skill in the art to which this disclosure belongs.

The term "alkyl group" as used herein is a branched or unbranched saturated hydrocarbon group of 1 to 24 carbon atoms, such as methyl, ethyl, n propyl, isopropyl, n butyl, isobutyl, t butyl, pentyl, hexyl, heptyl, octyl, decyl, tetradecyl, hexadecyl, eicosyl, tetracosyl and the like. A "lower alkyl" group is an alkyl group containing from one to six carbon atoms.

The term "aryl group" as used herein is any carbon-based aromatic group including, but not limited to, benzene, naphthalene, etc. The term "aromatic" also includes "heteroaryl group," which is defined as an aromatic group that has at least one heteroatom incorporated within the ring of the aromatic group. Examples of heteroatoms include, but are not limited to, nitrogen, oxygen, sulfur, and phosphorus. The aryl group can be substituted or unsubstituted. The aryl group can be substituted with one or more groups including, but not limited to, alkyl, alkynyl, alkenyl, aryl, halide, nitro, amino, ester, ketone, aldehyde, hydroxy, carboxylic acid, or alkoxy.

The term "aralkyl" as used herein is an aryl group having an alkyl, alkynyl, or alkenyl group as defined above attached to the aromatic group. An example of an aralkyl group is a benzyl group.

The term "carbonate group" as used herein is represented by the formula OC(O)OR, where R can be hydrogen, an alkyl, alkenyl, alkynyl, aryl, aralkyl, cycloalkyl, halogenated alkyl, or heterocycloalkyl group described above.

The term "organic residue" defines a carbon containing residue, i.e., a residue comprising at least one carbon atom, and includes but is not limited to the carbon-containing groups, residues, or radicals defined hereinabove. Organic residues can contain various heteroatoms, or be bonded to another molecule through a heteroatom, including oxygen, nitrogen, sulfur, phosphorus, or the like. Examples of organic residues include but are not limited alkyl or substituted alkyls, alkoxy or substituted alkoxy, mono or di-substituted amino, amide groups, etc. Organic residues can preferably comprise 1 to 18 carbon atoms, 1 to 15, carbon atoms, 1 to 12 carbon atoms, 1 to 8 carbon atoms, 1 to 6 carbon atoms, or 1 to 4 carbon atoms. In a further aspect, an organic residue can comprise 2 to 18 carbon atoms, 2 to 15, carbon atoms, 2 to 12 carbon atoms, 2 to 8 carbon atoms, 2 to 4 carbon atoms, or 2 to 4 carbon atoms.

A very close synonym of the term "residue" is the term "radical," which as used in the specification and concluding claims, refers to a fragment, group, or substructure of a molecule described herein, regardless of how the molecule is prepared. For example, a 2,4-dihydroxyphenyl radical in a particular compound has the structure:

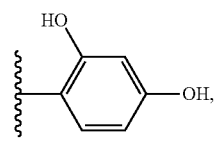

regardless of whether 2,4-dihydroxyphenyl is used to prepare the compound. In some embodiments the radical (for example an alkyl) can be further modified (i.e., substituted alkyl) by having bonded thereto one or more "substituent radicals." The number of atoms in a given radical is not critical to the present disclosure unless it is indicated to the contrary elsewhere herein.

"Organic radicals," as the term is defined and used herein, contain one or more carbon atoms. An organic radical can have, for example, 1-26 carbon atoms, 1-18 carbon atoms, 1-12 carbon atoms, 1-8 carbon atoms, 1-6 carbon atoms, or 1-4 carbon atoms. In a further aspect, an organic radical can have 2-26 carbon atoms, 2-18 carbon atoms, 2-12 carbon atoms, 2-8 carbon atoms, 2-6 carbon atoms, or 2-4 carbon atoms. Organic radicals often have hydrogen bound to at least some of the carbon atoms of the organic radical. One example, of an organic radical that comprises no inorganic atoms is a 5,6,7,8-tetrahydro-2-naphthyl radical. In some embodiments, an organic radical can contain 1-10 inorganic heteroatoms bound thereto or therein, including halogens, oxygen, sulfur, nitrogen, phosphorus, and the like. Examples of organic radicals include but are not limited to an alkyl, substituted alkyl, cycloalkyl, substituted cycloalkyl, mono-substituted amino, di-substituted amino, acyloxy, cyano, carboxy, carboalkoxy, alkylcarboxamide, substituted alkylcarboxamide, dialkylcarboxamide, substituted dialkylcarboxamide, alkylsulfonyl, alkylsulfinyl, thioalkyl, thiohaloalkyl, alkoxy, substituted alkoxy, haloalkyl, haloalkoxy, aryl, substituted aryl, heteroaryl, heterocyclic, or substituted heterocyclic radicals, wherein the terms are defined elsewhere herein. A few non-limiting examples of organic radicals that include heteroatoms include alkoxy radicals, trifluoromethoxy radicals, acetoxy radicals, dimethylamino radicals and the like.

As used herein, the terms "number average molecular weight" or "$M_n$," can be used interchangeably, and refer to the statistical average molecular weight of all the polymer chains in the sample and is defined by the formula:

$$M_n = \frac{\sum N_i M_i}{\sum N_i}, M_n = \frac{\sum N_i M_i}{\sum N_i},$$

where $M_i$ is the molecular weight of a chain and $N_i$ is the number of chains of that molecular weight. $M_n$ can be determined for polymers, e.g., polycarbonate polymers, by methods well known to a person having ordinary skill in the art using molecular weight standards, e.g. polycarbonate standards or polystyrene standards, preferably certified or traceable molecular weight standards.

$$M_n = \frac{\sum N_i M_i}{\sum N_i}.$$

As used herein, the terms "weight average molecular weight" or "Mw" can be used interchangeably, and are defined by the formula:

$$M_w = \frac{\sum N_i M_i^2}{\sum N_i M_i},$$

where $M_i$ is the molecular weight of a chain and $N_i$ is the number of chains of that molecular weight. Compared to $M_n$, $M_w$ takes into account the molecular weight of a given chain in determining contributions to the molecular weight average. Thus, the greater the molecular weight of a given chain, the more the chain contributes to the $M_w$. $M_w$ can be determined for polymers, e.g. polycarbonate polymers, by methods well known to a person having ordinary skill in the art using molecular weight standards, e.g. polycarbonate standards or polystyrene standards, preferably certified or traceable molecular weight standards.

As used herein, the terms "polydispersity index" or "PDI" can be used interchangeably, and are defined by the formula:

$$PDI = \frac{M_w}{M_n}.$$

The PDI has a value equal to or greater than 1, but as the polymer chains approach uniform chain length, the PDI approaches unity.

As used herein, "polycarbonate" refers to an oligomer or polymer comprising residues of one or more dihydroxy compounds, e.g., dihydroxy aromatic compounds, joined by carbonate linkages; it also encompasses homopolycarbonates, copolycarbonates, and (co)polyester carbonates.

The terms "residues" and "structural units", used in reference to the constituents of the polymers, are synonymous throughout the specification.

As used herein the terms "weight percent," "wt %," and "wt. %," which can be used interchangeably, indicate the percent by weight of a given component based on the total weight of the composition, unless otherwise specified. That is, unless otherwise specified, all wt % values are based on the total weight of the composition. It should be understood that the sum of wt % values for all components in a disclosed composition or formulation are equal to 100.

Each of the materials disclosed herein are either commercially available and/or the methods for the production thereof are known to those of skill in the art.

It is understood that the compositions disclosed herein have certain functions. Disclosed herein are certain structural requirements for performing the disclosed functions, and it is understood that there are a variety of structures that can perform the same function that are related to the disclosed structures, and that these structures will typically achieve the same result.

The terms "BisA," "BPA," or "bisphenol A," which can be used interchangeably, as used herein refers to a compound having a structure represented by the formula:

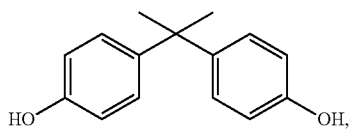

BisA can also be referred to by the name 4,4'-(propane-2,2-diyl)diphenol; p,p'-isopropylidenebisphenol; or 2,2-bis(4-hydroxyphenyl)propane. BisA has the CAS #80-05-7.

The term "promoter" as used herein refers to mercato carboxylic acids

The term "binding energy" as used herein refers to the binding energy (BE) as determined using the formula: BE=Energy (complex)−[Energy(cavity)+Energy(monomer)], where the energy corresponds to electronic energy of the system—e.g., monomer, cavity, and complex. In a further aspect, the energies of the cavity and monomer are calculated in the gas phase in vacuum. In a still further aspect, the complex described in the above equation corresponds to the energy of the optimized structure of the monomer in the constrained structure of the cavity. In some aspects, the calculations are performed using density functional theory (DFT) approach with 6-31G* basis set and B3-LYP functional as described above. The detailed procedure for calculating the binding energies of the monomers and estradiol to the estradiol related receptors a is described in U.S. patent application Ser. No. 14/284,040.

The term "half maximal inhibitory concentration" ($IC_{50}$) as used herein is a quantitative measure that indicates how much of a particular substance, i.e., an inhibitor, is needed to inhibit a given biological process or component of a process, by one half. In other words, it is the half maximal (50%) inhibitory concentration (IC) of a substance (50% IC, or $IC_{50}$). It is commonly known to one of ordinary skill in the art and used as a measure of antagonist drug potency in pharmacological research. The ($IC_{50}$) of a particular substance can be determined using conventional competition binding assays. In this type of assay, a single concentration of radioligand (such as an agonist) is used in every assay tube. The ligand is used at a low concentration, usually at or below its $K_d$ value. The level of specific binding of the radioligand is then determined in the presence of a range of concentrations or other competing non-radioactive compounds (usually antagonists), in order to measure the potency with which they compete for the binding of the radioligand. Competition curves may also be computer-fitted to a logistic function as described under direct fit. The $IC_{50}$ is the concentration of competing ligand which displaces 50% of the specific binding of the radioligand.

B. PHP MONOMER

In accordance with the purpose(s) of the disclosure, as embodied and broadly described herein, the disclosure, in one aspect, relates to ortho aryl substituted bisphenol monomers demonstrating a low affinity to estradiol related receptor (ERR)-α while still useful in the production of polymers. In further aspects, the ortho aryl substituted bisphenol monomer is PHP.

1. Structure

In various aspects, the present disclosure relates to methods for preparing a 2,2-bis(3-phenyl-4-hydroxyphenyl) propane (PHP) monomer. In further aspects, the PHP monomer has a structure represented by the formula:

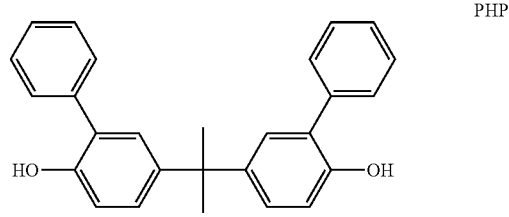 [SMILES: CC(C)(c1ccc(O)c(-c2ccccc2)c1)c1ccc(O)c(-c2ccccc2)c1]

In various aspects, this general class of monomers is known as aromatic dihydroxy compounds.

C. PREPARATION OF THE PHP MONOMER

In various aspects, the present disclosure provides a method for preparing an ortho aryl substituted bisphenol monomers, the method comprising: a) providing a phenol; b) providing a ketone; and c) reacting the phenol and ketone under conditions effective to provide a reaction product comprising an ortho aryl substituted bisphenol monomers, wherein the monomer exhibits a lower binding energy than estradiol for estradiol related receptor (ERR)-α obtained from the computational method described herein.

In further aspects, the phenol comprises 2-phenylphenol.

In some aspects, the 2-phenylphenol is a bio-based material. In further aspects, the phenol derived from a biological material. In some aspects, the phenol is wholly derived from a biological material. In other aspects, the phenol is partly derived from a biological material. In further aspects, the phenol not derived from organic material that has been transformed by geological processes into petroleum, petrochemicals, and combinations thereof. In further aspects, the phenol is from greater than 0 wt. % to about 100 wt. % derived from bio-based material, including exemplary values of 1 wt. %, 5 wt. %, 10 wt. %, 20 wt. %, 30 wt. %, 40 wt. %, 50 wt. %, 60 wt. %, 70 wt. %, 80 wt. %, 90 wt. %, and 99 wt. % derived from bio-based material. In still further aspects, the bio-based material comprises at least one lignocellulosic material, plant material, or a combination thereof.

In further aspects, the ketone is acetone.

In various aspects, the 2-phenylphenol and acetone are provided at a ratio of at least about 2:1. In further aspects, the 2-phenylphenol and acetone are provided at a ratio of at least about 3:1. In still further aspects, the 2-phenylphenol and acetone are provided at a ratio of from about 2:1 to about 6:1, including exemplary ratios of 3:1, 4:1, and 5:1.

In further aspects, the phenol and ketone are provided at a ratio of at least about 2:1. In still further aspects, the phenol and ketone are provided at a ratio of from about 2:1 to about 6:1, including exemplary ratios of 3:1, 4:1, and 5:1.

In further aspects, conditions effective comprise reacting the phenol and ketone in the presence of a catalyst. In still further aspects, the catalyst can comprise $H_2SO_4$, an cationic acidic ion exchange resin or sulfonated polystyrene resin cross linked with divinyl benzene catalyst, dodecyl benzene sulfonic acid (DBSA), trifluoro acetic acid, toluene sulfonic acid, trifluromethane sulfonic acid, HCl, or a combination thereof. In yet further aspects, conditions effective comprise reacting the phenol and acetone in the presence of 3-mercaptopropionic acid (3-MPA) as promoter. In some aspects, the catalyst is $H_2SO_4$, an cationic acidic ion exchange resin or sulfonated polystyrene resin cross linked with divinyl benzene, $C_1$-$C_{24}$ alkyl or alkyl aryl sulfonic acid, HCl, or a combination thereof. In other aspects, the catalyst is concentrated HCl.

In further aspects, conditions effective comprise reacting the 2-phenylphenol and acetone in the presence of a catalyst. In still further aspects, the catalyst can comprise $H_2SO_4$, an cationic acidic ion exchange resin or sulfonated polystyrene resin cross linked with divinyl benzene catalyst, dodecyl benzene sulfonic acid (DBSA), trifluoro acetic acid, toluene sulfonic acid, trifluromethane sulfonic acid, HCl, or a combination thereof. In some aspects, the catalyst is $H_2SO_4$, an cationic acidic ion exchange resin or sulfonated polystyrene resin cross linked with divinyl benzene, C1-C24 alkyl or alkyl aryl sulfonic acid, HCl, or a combination thereof. In other aspects, the catalyst is HCl gas. In some other aspects the catalyst is a solid acid catalyst such as sulfonated Zirconia, Acidified clays, or combination thereof.

In yet further aspects, conditions effective comprise reacting the phenol and acetone in the presence of a promoter. In other aspects, the promoter is a compound containing a mercapto group including alkylmercaptans such as emthylmercaptan, ethylmercaptan, propylmercaptan, butylmercaptan, octylmercaptan, dodecylmercaptan, propylmercaptan, butylmercaptan, octylmercaptan, or dodecylmercaptan; or aromatic mercaptans such as thiophenol, or thiocresol; or mercapto organic acids such as mercapto acetic acid (thioglycolic acid), or mercaptopropionic acid. In yet further aspects, the promoter used with the acid catalyst is mercaptopropionic acid In some aspects the amount of promoter loading is generally in the range of 0.01 to 10% by weight to the total amount of phenol and ketone In further aspects, conditions effective comprise adjusting the temperature to at least about 50° C. In still further aspects, the temperature is adjusted to a temperature of from 50° C. to about 150° C., including exemplary temperatures of about 55, 60, 65, 70, 75, 80, 85, 90, 95, 100, 105, 110, 115, 120, 125, 130, 135, 140, and 145° C.

In further aspects, conditions effective comprise maintaining the reaction for at least about 4 hours. In yet further aspects, the reaction is maintained for about 3 to 10 hours, including exemplary times of 4, 5, 6, 7, 8 and 9 hours.

In further aspects, the dihydroxy aromatic monomer is an ortho aryl substituted bisphenol monomer. In still further aspects, the ortho aryl substituted bisphenol monomer is 2,2-bis(3-phenyl-4-hydroxyphenyl) propane (PHP).

In various aspects, the reaction product comprises at least about 10 wt. % of the dihydroxy aromatic monomer. In further aspects, the reaction product comprises from at least about 01 wt. % to about 100 wt. % of the ortho aryl substituted bisphenol monomer, including exemplary values of 20 wt. %, 25 wt. %, 30 wt. %, 35 wt. %, 40 wt. %, 45 wt. %, 50 wt. %, 55 wt. %, 60 wt. %, 65 wt. %, 70 wt. %, 75 wt. %, 80 wt. %, 85 wt. %, 90 wt. %, and 95 wt. %. In still further aspects, the reaction product comprises at least about 10 wt. % of PHP. In even further aspects, the reaction product comprises from at least about 10 wt. % to about 100 wt. % of PHP, including exemplary values of 20 wt. %, 25 wt. %, 30 wt. %, 35 wt. %, 40 wt. %, 45 wt. %, 50 wt. %, 55 wt. %, 60 wt. %, 65 wt. %, 70 wt. %, 75 wt. %, 80 wt. %, 85 wt. %, 90 wt. %, and 95 wt. %.

In various aspects, the disclosure provides a method for preparing an ortho aryl substituted bisphenol monomer, the method comprising: a) providing 2-phenylphenol; b) providing acetone; and c) reacting the 2-phenylphenol and acetone under reaction conditions effective to provide a reaction product comprising 2,2-bis(3-phenyl-4-hydroxyphenyl) propane (PHP); wherein PHP exhibits a lower binding energy than estradiol with estradiol related receptors (ERR) α.

In further aspects, the compounds of this disclosure can be prepared through the reactions as set forth in the disclosed schemes as well as in other standard manipulations known in the literature, exemplified in the experimental sections, or apparent to one skilled in the art.

Without further elaboration, it is believed that one skilled in the art can, using the description herein, utilize the present disclosure. The following examples are included to provide addition guidance to those skilled in the art of practicing the claimed disclosure. The examples provided are merely representative of the work and contribute to the teaching of the present disclosure. Accordingly, these examples are not intended to limit the disclosure in any manner. Thus, each disclosed method can further comprise additional steps, manipulations, and or components.

Synthesis Scheme

In various aspects, the ortho aryl substituted bisphenol monomers, as disclosed herein, can generically be prepared according to one or more reaction schemes, as shown below. In further aspects, 2-phenylphenol and acetone can be condensed in the presence of a catalyst and a promoter to yield PHP.

a. Synthesis Route 1

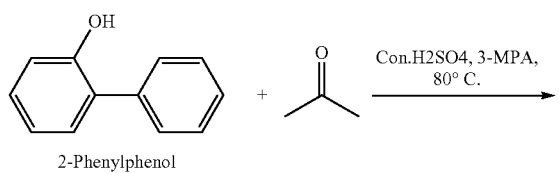

2-Phenylphenol

-continued

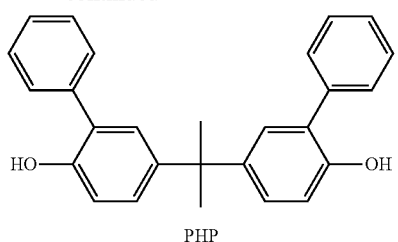

PHP

As shown in Route 1, 2-phenylphenol and acetone (3:1) are reacted in the presence of concentrated $H_2SO_4$ as an acid catalyst and 3-mercaptoacetic acid as a promoter to provide PHP.

b. Synthesis Route 2

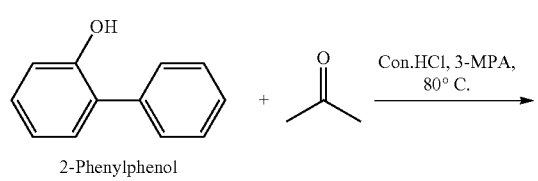

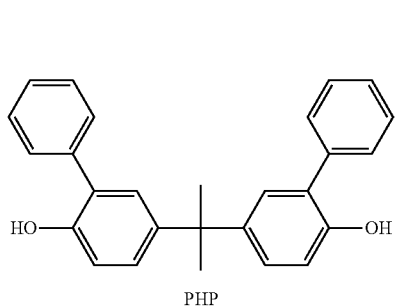

PHP

As shown in Route 2, 2-phenylphenol and acetone (3:1) are reacted in the presence of concentrated HCl as a catalyst and mercaptopropionic acid as a promoter to provide PHP.

c. Synthesis Route 3

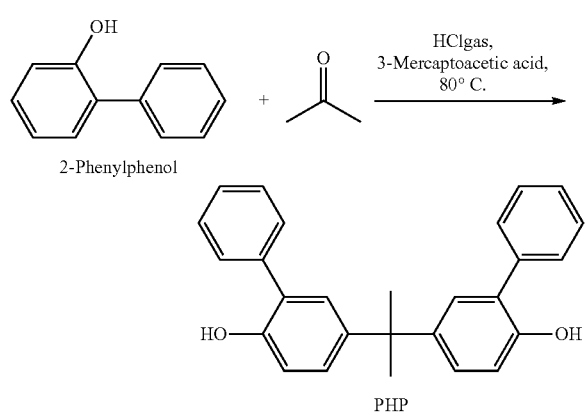

PHP

As shown in Route 3, 2-phenylphenol and acetone (3:1) are reacted in the presence of HCl gas, as a catalyst, and 3-mercaptoacetic acid, as a promoter, to provide PHP.

d. Synthesis Route 4

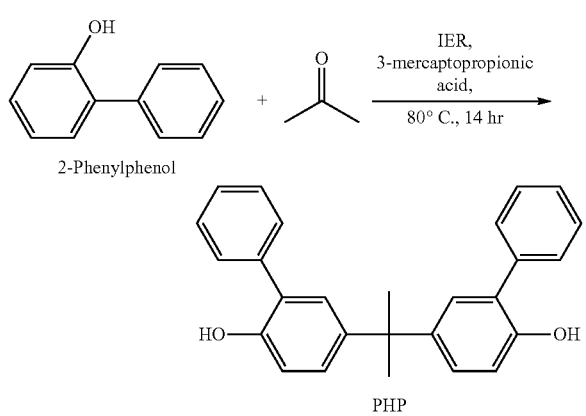

PHP

As shown in Route 4, 2-phenylphenol and acetone (3:1) are reacted in the presence of IER (Ion exchange resin) as a catalyst, and 3-mercaptopropionic acid, as a promoter, to provide PHP e. Synthesis Route 5

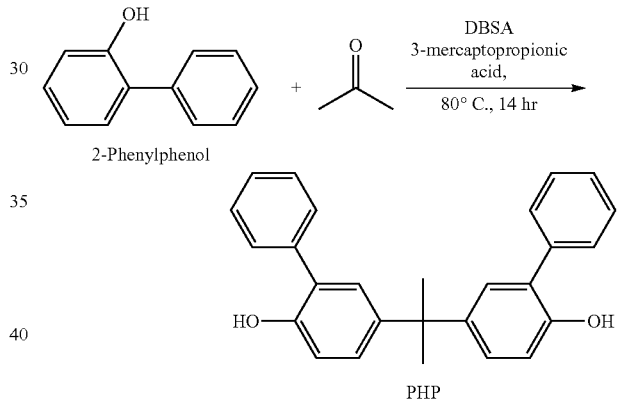

PHP

As shown in Route 5, 2-phenylphenol and acetone (3:1) are reacted in the presence of DBSA (Dodecyl Benzene Sulfonic acid) as a catalyst, and 3-mercaptopropionic acid, as a promoter, to provide PHP.

From Route 1, 20% of PHP was formed, whereas Route 2 provided a maximum 90% of PHP, Route 3 provided 50% of PHP, Route 4 provided 10% PHP, and Route 5 provided 10% PHP While aspects of the present disclosure can be described and claimed in a particular statutory class, such as the system statutory class, this is for convenience only and one of skill in the art will understand that each aspect of the present disclosure can be described and claimed in any statutory class. Unless otherwise expressly stated, it is in no way intended that any method or aspect set forth herein be construed as requiring that its steps be performed in a specific order. Accordingly, where a method claim does not specifically state in the claims or descriptions that the steps are to be limited to a specific order, it is no way intended that an order be inferred, in any respect. This holds for any possible non-express basis for interpretation, including matters of logic with respect to arrangement of steps or operational flow, plain meaning derived from grammatical organization or punctuation, or the number or type of aspects described in the specification.

D. PREPARATION OF POLYCARBONATES FROM THE PHP MONOMER

In various aspects, the disclosed ortho aryl substituted bisphenol monomers are useful for making polycarbonate polymers and thermoplastic compositions.

In one aspect, the thermoplastic compositions comprise a polycarbonate polymer composition wherein the polycarbonate polymer comprises PHP, a polycarbonate copolymer, or combinations thereof.

In one aspect, a polycarbonate can comprise any polycarbonate material or mixture of materials, for example, as recited in U.S. Pat. No. 7,786,246, which is hereby incorporated in its entirety for the specific purpose of disclosing various polycarbonate compositions and methods. The term polycarbonate can be further defined as compositions have repeating structural units of the formula (1):

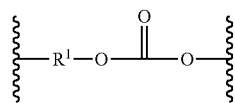

(1)

in which at least 60 percent of the total number of $R^1$ groups are aromatic organic radicals and the balance thereof are aliphatic, alicyclic, or aromatic radicals. In a further aspect, each $R^1$ is an aromatic organic radical and, more preferably, a radical of the formula (2):

$$-A^1-Y^1-A^2- \quad (2),$$

wherein each of $A^1$ and $A^2$ is a monocyclic divalent aryl radical and $Y^1$ is a bridging radical having one or two atoms that separate $A^1$ from $A^2$. In various aspects, one atom separates $A^1$ from $A^2$. For example, radicals of this type include, but are not limited to, radicals such as —O—, —S—, —S(O)—, —S(O$_2$)—, —C(O)—, methylene, cyclohexyl-methylene, 2-[2.2.1]-bicycloheptylidene, ethylidene, isopropylidene, neopentylidene, cyclohexylidene, cyclopentadecylidene, cyclododecylidene, and adamantylidene. The bridging radical $Y^1$ is preferably a hydrocarbon group or a saturated hydrocarbon group such as methylene, cyclohexylidene, or isopropylidene.

In a further aspect, polycarbonates can be produced by the interfacial reaction of dihydroxy compounds having the formula HO—$R^1$—OH, which includes dihydroxy compounds of formula (3):

$$HO-A^1-Y^1-A^2-OH \quad (3),$$

wherein $Y^1$, $A^1$ and $A^2$ are as described above. Also included are bisphenol compounds of general formula (4):

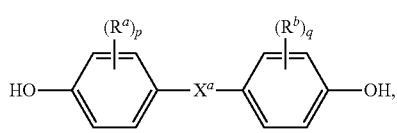

(4)

wherein $R^a$ and $R^b$ each represent an alkoxy group, or a monovalent hydrocarbon group and can be the same or different; p and q are each independently integers from 0 to 4; and $X^a$ represents one of the groups of formula (5):

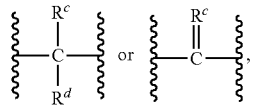

(5)

wherein $R^c$ and $R^d$ each independently represent a hydrogen atom or a monovalent linear or cyclic hydrocarbon group and $R^e$ is a divalent hydrocarbon group.

In further aspects, the ortho aryl substituted bisphenol monomer does not demonstrate a binding energy greater than or equal to about −20.37 kcal/mol which correspond to the estradiol to the ligand binding domain cavity of the estradiol related receptor (ERR)-α. In still other aspects, the ortho aryl substituted bisphenol monomers exhibits binding energy lower than the estradiol in the ligand binding domain cavity of the estradiol related receptor α.

In some aspects of the disclosure, suitable aromatic dihydroxy monomers comprise phenolic monomers. In further aspects, the phenolic monomers can comprise dihydric phenols, mono phenols, bisphenols, or a combination thereof.

In some aspects, the aromatic dihydroxy monomer is a bisphenolic monomer. In further aspects, the bisphenol monomer is an ortho aryl substituted bisphenol monomer. In still further aspects, the ortho aryl substituted bisphenol monomer is 2,2-bis(3-phenyl-4-hydroxyphenyl) propane, and has a structure represented by the formula:

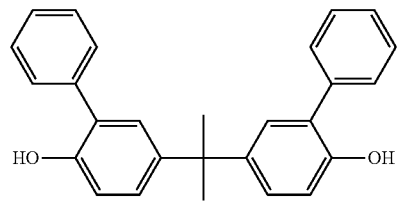 [SMILES: CC(C)(c1ccc(O)c(-c2ccccc2)c1)c1ccc(O)c(-c2ccccc2)c1]

According to aspects of the disclosure, any additional suitable aromatic dihydroxy monomers exhibiting a reduced estradiol related receptor binding activity (e.g., characterized by a lower binding energy with respect to the estradiol) as described above may be used.

In addition to the polycarbonates described above, combinations of the polycarbonate with other thermoplastic polymers, for example combinations of homopolycarbonates and/or polycarbonate copolymers, can be used.

In some aspects, the polycarbonate can be a co-polycarbonate comprising repeating carbonate units derived from an ortho alkyl bisphenol monomer and at least one additional phenolic monomer.

In some aspects, the polycarbonate is a poly(ester carbonate) comprising repeating carbonate units derived from the ortho alkoxy bisphenol monomer and at least one dicarboxylic acid monomer. In various further aspects, the polycarbonate can employ two or more different dihydroxy compounds or a copolymer of a dihydroxy compounds with a glycol or with a hydroxy- or acid-terminated polyester or with a dibasic acid or hydroxy acid in the event a carbonate copolymer rather than a homopolymer is desired for use. Polyarylates and polyester-carbonate resins or their blends can also be employed. Branched polycarbonates are also useful, as well as blends of linear polycarbonate and a branched polycarbonate. The branched polycarbonates can be prepared by adding a branching agent during polymerization.

In a further aspect, the branching agents include polyfunctional organic compounds containing at least three functional groups selected from hydroxyl, carboxyl, carboxylic anhydride, haloformyl, and mixtures thereof. Specific examples include trimellitic acid, trimellitic anhydride, trimellitic trichloride, tris-p-hydroxy phenyl ethane, isatin-bis-phenol, tris-phenol TC (1,3,5-tris((p-hydroxyphenyl)isopropyl)benzene), tris-phenol PA (4(4(1,1-bis(p-hydroxyphenyl)-ethyl) alpha, alpha-dimethyl benzyl)phenol), 4-chloroformyl phthalic anhydride, trimesic acid, and benzophenone tetracarboxylic acid. The branching agents can be added at a level of from 0.05-2.0 weight percent. Branching agents and procedures for making branched polycarbonates are described in U.S. Pat. Nos. 3,635,895 and 4,001,184. All types of polycarbonate end groups are contemplated as being useful in the thermoplastic composition.

In a further aspect, the polycarbonate can be a linear homopolymer derived from an ortho aryl substituted bisphenol monomer, in which each of $A^1$ and $A^2$ is PHP and $Y^1$ is isopropylidene. The polycarbonates generally can have an intrinsic viscosity, as determined in chloroform at 25° C., of 0.3 to 1.5 deciliters per gram (dl/g), specifically 0.45 to 1.0 dl/g. The polycarbonates can have a weight average molecular weight (Mw) of 10,000 to 100,000 g/mol, as measured by gel permeation chromatography (GPC) using a crosslinked styrene-divinyl benzene column, at a sample concentration of 1 milligram per milliliter, and as calibrated with polycarbonate standards.

In a further aspect, a polycarbonate component used in the present disclosure can have a melt volume flow rate (often abbreviated MVR) measures the rate of extrusion of a thermoplastics through an orifice at a prescribed temperature and load. Polycarbonates useful for the formation of articles can have an MVR, measured at 300° C. under a load of 1.2 kg according to ASTM D1238-04 or ISO 1133, of 0.5 to 80 cubic centimeters per 10 minutes (cc/10 min). In a still further aspect, the polycarbonate comprises two polycarbonate polymers wherein one of the polycarbonate polymers is a poly(aliphatic ester)-polycarbonate. In cases where the polycarbonate components comprises a non-poly(aliphatic ester)-polycarbonate and a poly(aliphatic ester)-polycarbonate, the non-poly(aliphatic ester)-polycarbonate (or a combination of such polycarbonates) can have a MVR measured at 300° C. under a load of 1.2 kg according to ASTM D1238-04 or ISO 1133, of 45 to 75 cc/10 min, specifically 50 to 70 cc/10 min, and more specifically 55 to 65 cc/10 min.

In a further aspect, the polycarbonate can be a linear homopolymer derived from an ortho aryl substituted bisphenol monomer, in which each of $A^1$ and $A^2$ is PHP and $Y^1$ is isopropylidene. The polycarbonates generally can have an intrinsic viscosity, as determined in chloroform at 25° C., of 0.3 to 1.5 deciliters per gram (dl/g), specifically 0.45 to 1.0 dl/g. The polycarbonates can have a weight average molecular weight (Mw) of 10,000 to 100,000 g/mol, as measured by gel permeation chromatography (GPC) using a crosslinked styrene-divinyl benzene column, at a sample concentration of 1 milligram per milliliter, and as calibrated with polycarbonate standards.

In a further aspect, a polycarbonate component used in the present disclosure can have a melt volume flow rate (often abbreviated MVR) measures the rate of extrusion of a thermoplastics through an orifice at a prescribed temperature and load. Polycarbonates useful for the formation of articles can have an MVR, measured at 300° C. under a load of 1.2 kg according to ASTM D1238-04 or ISO 1133, of 0.5 to 80 cubic centimeters per 10 minutes (cc/10 min). In a still further aspect, the polycarbonate comprises two polycarbonate polymers wherein one of the polycarbonate polymers is a poly(aliphatic ester)-polycarbonate. In cases where the polycarbonate components comprises a non-poly(aliphatic ester)-polycarbonate and a poly(aliphatic ester)-polycarbonate, the non-poly(aliphatic ester)-polycarbonate (or a combination of such polycarbonates) can have a MVR measured at 300° C. under a load of 1.2 kg according to ASTM D1238-04 or ISO 1133, of 45 to 75 cc/10 min, specifically 50 to 70 cc/10 min, and more specifically 55 to 65 cc/10 min.

In one aspect, an end-capping agent (also referred to as a chain-stopper) can optionally be used to limit molecular weight growth rate, and so control molecular weight in the polycarbonate. In various aspects, many conventionally known end capping agents exhibit undesirably high levels of estradiol binding activity. In contrast, however, suitable end capping agents or chain stoppers for use with the present disclosure exhibit estradiol binding activity levels similar or even identical to that of the selected ortho aryl substituted bisphenol monomers.

In another aspect, endgroups can be derived from the carbonyl source (i.e., the diaryl carbonate), from selection of monomer ratios, incomplete polymerization, chain scission, and the like, as well as any added end-capping groups, and can include derivatizable functional groups such as hydroxy groups, carboxylic acid groups, or the like. In one aspect, the endgroup of a polycarbonate, including a polycarbonate polymer as defined herein, can comprise a structural unit derived from a diaryl carbonate, where the structural unit can be an endgroup. In a further aspect, the endgroup is derived from an activated carbonate. Such endgroups can be derived from the transesterification reaction of the alkyl ester of an appropriately substituted activated carbonate, with a hydroxy group at the end of a polycarbonate polymer chain, under conditions in which the hydroxy group reacts with the ester carbonyl from the activated carbonate, instead of with the carbonate carbonyl of the activated carbonate. In this way, structural units derived from ester containing compounds or substructures derived from the activated carbonate and present in the melt polymerization reaction can form ester endgroups.

In one aspect, the melt polymerization reaction can be conducted by subjecting the reaction mixture to a series of temperature-pressure-time protocols. In some aspects, this involves gradually raising the reaction temperature in stages while gradually lowering the pressure in stages. In one aspect, the pressure is reduced from about atmospheric pressure at the start of the reaction to about 1 millibar (100 Pa) or lower, or in another aspect to 0.1 millibar (10 Pa) or lower in several steps as the reaction approaches completion. The temperature can be varied in a stepwise fashion beginning at a temperature of about the melting temperature of the reaction mixture and subsequently increased to final temperature. In one aspect, the reaction mixture is heated from room temperature to about 150° C. In such an aspect, the polymerization reaction starts at a temperature of about 150° C. to about 220° C. In another aspect, the polymerization temperature can be up to about 220° C. In other aspects, the polymerization reaction can then be increased to about 250° C. and then optionally further increased to a temperature of about 320° C., and all subranges there between. In one aspect, the total reaction time can be from about 30 minutes to about 200 minutes and all subranges there between. This procedure will generally ensure that the reactants react to give polycarbonates with the desired molecular weight, glass transition temperature and physical properties. The reaction proceeds to build the polycarbonate chain with production of ester-substituted alcohol by-product such as methyl salicylate. In one aspect, efficient removal of the by-product can be achieved by different techniques such as reducing the pressure. Generally the pressure starts relatively high in the beginning of the reaction and is lowered progressively throughout the reaction and temperature is raised throughout the reaction.

In one aspect, the progress of the reaction can be monitored by measuring the melt viscosity or the weight average molecular weight of the reaction mixture using techniques known in the art such as gel permeation chromatography. These properties can be measured by taking discrete samples or can be measured on-line. After the desired melt viscosity and/or molecular weight is reached, the final polycarbonate product can be isolated from the reactor in a solid or molten form. It will be appreciated by a person skilled in the art, that the method of making aliphatic homopolycarbonate and aliphatic-aromatic copolycarbonates as described in the preceding sections can be made in a batch or a continuous process and the process disclosed herein is preferably carried out in a solvent free mode. Reactors chosen should ideally be self-cleaning and should minimize any "hot spots." However, vented extruders similar to those that are commercially available can be used.

Polycarbonates, including polyester-polycarbonates, can be also be manufactured by interfacial polymerization. Although the reaction conditions for interfacial polymerization can vary, an exemplary process generally involves dissolving or dispersing a dihydric phenol reactant in aqueous caustic soda or potash, adding the resulting mixture to a suitable water-immiscible solvent medium, and contacting the reactants with a carbonate precursor in the presence of a catalyst such as triethylamine or a phase transfer catalyst, under controlled pH conditions, e.g., about 8 to about 10. The most commonly used water immiscible solvents include methylene chloride, 1,2-dichloroethane, chlorobenzene, toluene, and the like.

Carbonate precursors include, for example, a carbonyl halide such as carbonyl bromide or carbonyl chloride, or a haloformate such as a bishaloformates of a dihydric phenol (e.g., the bischloroformates of bisphenol A, hydroquinone, or the like) or a glycol (e.g., the bishaloformate of ethylene glycol, neopentyl glycol, polyethylene glycol, or the like). Combinations comprising at least one of the foregoing types of carbonate precursors can also be used. In an exemplary aspect, an interfacial polymerization reaction to form carbonate linkages uses phosgene as a carbonate precursor, and is referred to as a phosgenation reaction.

An effective amount of a phase transfer catalyst can be about 0.1 to about 10 wt % based on the weight of bisphenol in the phosgenation mixture. In another aspect, an effective amount of phase transfer catalyst can be about 0.5 to about 2 wt % based on the weight of bisphenol in the phosgenation mixture.

In various aspects, the polycarbonate comprises at least one polycarbonate polymer, wherein the polycarbonate polymer can be a homopolymer, a copolymer, or combinations thereof. In a further aspect, the polycarbonate comprises two or more polycarbonate polymers. In a still further aspect, the polycarbonate comprises three or more polycarbonate polymers. In a yet further aspect, the polycarbonate is a blend of at least two polycarbonate polymers.

In a further aspect, the polycarbonate is a homopolymer. In a still further aspect, the polycarbonate is a homopolymer comprising repeating units derived from 2,2-bis(3-phenyl-4-hydroxyphenyl) propane.

In a further aspect, the polycarbonate is a copolymer. In a still further aspect, the polycarbonate is a copolymer comprising repeating units derived from PHP. In yet a further aspect, the polycarbonate is a copolymer comprising repeating units derived from sebacic acid. In an even further aspect, the polycarbonate is a copolymer comprising repeating units derived from sebacic acid and PHP.

In various aspects, the disclosed thermoplastic compositions further comprise at least one additive material ordinarily incorporated in polycarbonate resin compositions of this type, with the proviso that the additives are selected so as to not significantly adversely affect the desired properties of the polycarbonate composition. Combinations of additives can be used. Such additives can be mixed at a suitable time during the mixing of the components for forming the composition. Exemplary and non-limiting examples of additive materials that can be present in the disclosed polycarbonate compositions include an acid scavenger, anti-drip agent, antioxidant, antistatic agent, chain extender, colorant (e.g., pigment and/or dye), de-molding agent, flow promoter, lubricant, mold release agent, plasticizer, quenching agent, stabilizer (including for example, a thermal stabilizer, a hydrolytic stabilizer, or a light stabilizer), or UV additive (including for example, absorbing additive or UV reflecting additive), or a combination thereof.

In various aspects, plasticizers, lubricants, and/or mold release agents additives can also be used. There is a considerable overlap among these types of materials, which include, for example, phthalic acid esters such as dioctyl-4,5-epoxy-hexahydrophthalate; tris(octoxycarbonylethyl)isocyanurate; tristearin; di- or polyfunctional aromatic phosphates such as resorcinol tetraphenyl diphosphate (RDP), the bis(diphenyl) phosphate of hydroquinone and the bis(diphenyl)phosphate of bisphenol-A; poly-alpha-olefins; epoxidized soybean oil; silicones, including silicone oils; esters, for example, fatty acid esters such as alkyl stearyl esters, e.g. methyl stearate; stearyl stearate, pentaerythritol tetrastearate, and the like; mixtures of methyl stearate and hydrophilic and hydrophobic nonionic surfactants comprising polyethylene glycol polymers, polypropylene glycol polymers, and copolymers thereof; waxes such as beeswax, montan wax, paraffin wax or the like.

In a further aspect, the anti-drip agents can also be present. In a further aspect, the anti-drip agent is a styrene-acrylonitrile copolymer encapsulated polytetrafluoroethylene. Exemplary anti-drip agents can include a fibril forming or non-fibril forming fluoropolymer such as polytetrafluoroethylene (PTFE). The anti-drip agent can optionally be encapsulated by a rigid copolymer, for example styrene-acrylonitrile (SAN). PTFE encapsulated in SAN is known as TSAN. Encapsulated fluoropolymers can be made by polymerizing the encapsulating polymer in the presence of the fluoropolymer, for example, in an aqueous dispersion. TSAN can provide significant advantages over PTFE, in that TSAN can be more readily dispersed in the composition. A suitable TSAN can comprise, for example, about 50 wt % PTFE and about 50 wt % SAN, based on the total weight of the encapsulated fluoropolymer. Alternatively, the fluoropolymer can be pre-blended in some manner with a second polymer, such as for, example, an aromatic polycarbonate resin or SAN to form an agglomerated material for use as an anti-drip agent. Either method can be used to produce an encapsulated fluoropolymer.

In various aspects, the thermoplastic compositions of the present disclosure can further comprise an acid or an acid salt. In one aspect, the acid or acid salt is an inorganic acid or inorganic acid salt. In one aspect, the acid is an acid including a phosphorous containing oxy-acid. In one aspect, the phosphorous containing oxy-acid is a multi-protic phosphorus containing oxy-acid having the general formula:

$$H_mP_tO_n,$$

where m and n are each 2 or greater and t is 1 or greater. Examples of the acids of the foregoing formula include, but are not limited to, acids represented by the following formulas: $H_3PO_4$, $H_3PO_3$, and $H_3PO_2$. Other exemplary acids include phosphoric acid, phosphorous acid, hypophosphorous acid, hypophosphoric acid, phosphinic acid, phosphonic acid, metaphosphoric acid, hexametaphosphoric acid, thiophosphoric acid, fluorophosphoric acid, difluorophosphoric acid, fluorophosphorous acid, difluorophosphorous acid, fluorohypophosphorous acid, or fluorohypophosphoric acid. Alternatively, acids and acid salts, such as, for example, sulphuric acid, sulphites, mono zinc phosphate, mono calcium phosphate, sodium acid pyrophosphate, mono natrium phosphate, and the like, can be used. The acid or acid salt is selected so that it can be effectively combined with the filler to produce a synergistic effect and a balance of properties, such as flow and impact, in the polycarbonate or polycarbonate blend.

E. ARTICLES OF MANUFACTURE

In one aspect, the present disclosure pertains to shaped, formed, or molded articles comprising the disclosed PHP monomers and thermoplastic compositions. The thermoplastic compositions can be molded into useful shaped articles by a variety of means such as injection molding, extrusion, rotational molding, blow molding and thermoforming to form articles. The thermoplastic compositions described herein can also be made into film and sheet as well as components of laminate systems. In a further aspect, a method of manufacturing an article comprises melt blending the polycarbonate component, and any additional components; and molding the extruded composition into an article. In a still further aspect, the extruding is done with a twin-screw extruder.

In a further aspect, the article is molded. In a still further aspect, the article is extrusion molded. In yet a further aspect, the article is injection molded.

The compositions of the present disclosure are well suited for a variety of uses, including various articles of manufacture. For example, and without limitation, the compositions of the disclosure can be used for medical devices, food service uses, housewares, electronics, packaging, computer enclosures, trays, drinking glasses, pitchers, eye glasses, syringes, connectors, cell phone housings, keycaps, handles, bottles, films, coatings, and the like.

In some aspects, the article is selected from a medical device, surgical device, imaging device, monitoring device, blood care device, drug delivery device, interior trim, window, floor, cover, wall panel, door, enclosure, housing, panel, lighting switch, bedding part, furniture part, culinary device, food preparation device, food storage device, or food delivery device, or a combination thereof.

In a further aspect, the resulting disclosed compositions can be used to provide any desired shaped, formed, or molded articles. For example, the disclosed compositions can be molded into useful shaped articles by a variety of means such as injection molding, extrusion, rotational molding, blow molding and thermoforming. As noted above, the disclosed compositions are particularly well suited for use in the manufacture of electronic components and devices. As such, according to some aspects, the disclosed compositions can be used to form articles such as printed circuit board carriers, burn in test sockets, flex brackets for hard disk drives, and the like.

F. ASPECTS

The disclosed compositions and methods include at least the following aspects.

Aspect 1: An aromatic dihydroxy compound monomer prepared by reacting a ketone and a phenol in the presence of concentrated hydrochloric acid and 3-mercaptoacetic acid, wherein the aromatic dihydroxy compound is an ortho aryl substituted bisphenol monomer, and wherein the aromatic dihydroxy compound has a lower binding energy than that of estradiol to the ligand binding domain cavity of an estradiol related receptor comprising ERR-α.

Aspect 2: The aromatic dihydroxy compound monomer of aspect 1, wherein the lower binding energy is determined using the formula: binding energy=energy (complex)−[energy(cavity)+energy(monomer)], wherein the energy (complex) is an electronic energy of an optimized monomer structure in a constrained structure of the ligand binding domain cavity of the estradiol related receptor, the energy (cavity) is an electronic energy of the ligand binding domain cavity of the estradiol related receptor, and the energy (monomer) is an electronic energy of the monomer.

Aspect 3: The aromatic dihydroxy compound monomer of aspect 1, wherein the ketone is acetone.

Aspect 4: The aromatic dihydroxy compound monomer of aspect 1, wherein the phenol is 2-phenylphenol.

Aspect 5: The aromatic dihydroxy compound monomer of aspect 1, wherein the concentrated hydrochloric acid is dry.

Aspect 6: The aromatic dihydroxy compound monomer of aspect 1, wherein the ketone and the phenol are reacted in a temperature range of from about 70° C. to about 90° C.

Aspect 7: The aromatic dihydroxy compound monomer of aspect 1, wherein the ketone and the phenol are reacted using a ratio of 3.0 mole of phenol to 1.0 mole of ketone.

Aspect 8: A polymer comprising at least one structural unit derived from the aromatic dihydroxy compound monomer of aspect 1.

Aspect 9: A method for preparing an ortho aryl substituted bisphenol monomer comprising: reacting a ketone and a phenol in the presence of concentrated hydrochloric acid and 3-mercaptopropionic acid to produce an aromatic dihydroxy compound, wherein the aromatic dihydroxy compound is an ortho aryl substituted bisphenol monomer, and wherein the aromatic dihydroxy compound has a lower binding energy than the binding energy of estradiol to the ligand binding domain cavity of an estradiol related receptor comprising ERR-α.

Aspect 10: The method of aspect 9, wherein the binding energy value is determined using the formula: binding energy=energy (complex)−[energy(cavity)+energy(monomer)], wherein energy (complex) is the electronic energy of the optimized monomer structure in the constrained structure of the ligand binding domain cavity of the estradiol related receptor, the energy (cavity) is the electronic energy of the cavity and the energy (monomer) is the electronic energy of the monomer.

Aspect 11: The method of aspect 9, wherein preparing an ortho aryl substituted bisphenol monomer is a batch or continuous process.

Aspect 12: The method of aspect 9, wherein the ketone is acetone.

Aspect 13: The method of aspect 9, wherein the phenol is 2-phenylphenol.

Aspect 14: The aromatic dihydroxy compound monomer of aspect 1, wherein the concentrated hydrochloric acid is dry.

Aspect 15: The method of aspect 9, wherein the phenol and ketone are reacted in the presence of an acidic catalyst.

Aspect 16: The method of aspect 15, wherein the acidic catalyst comprises $H_2SO_4$, an ion exchange resin catalyst, $C_1$-$C_{24}$ alkyl or alkyl aryl sulfonic acid, HCl, or a combination thereof.

Aspect 17: The method of aspect 9, wherein the phenol and ketone are provided at a molar ratio of at least about 2:1.

Aspect 18: The method of aspect 9, wherein the ketone and the phenol are reacted in a temperature range of from about 70° C. to about 90° C.

Aspect 19: The method of aspect 9, wherein the ketone and the phenol are reacted using a ratio of 3.0 mole of phenol to 1.0 mole of ketone.

Aspect 20: The method of aspect 9, wherein the selectivity of the reaction of the ketone and the phenol is 95:5.

Aspect 21: The method of aspect 9, wherein the conversion of the reaction of the ketone and the phenol is greater than about 50%.

Aspect 22: A method for the preparation of an ortho aryl substituted bisphenol monomer, represented by Formula I:

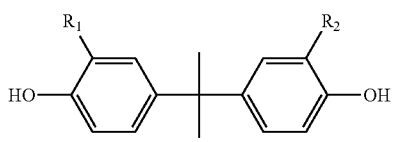

where $R_1$ and $R_2$=phenyl,
comprising: reacting a compound represented by Formula II:

with a compound represented by Formula III:

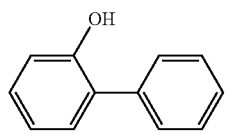

in the presence of an acid catalyst and promoter.

Aspect 23: The method of aspect 22, wherein the acid catalyst employed is concentrated hydrochloric acid and the compounds of Formula II and III are reacted with the acid and promoter at a temperature of about 70° C. to about 90° C.

Aspect 24: The method of aspect 22, wherein the promoter is 3-mercaptopropionic acid and the compounds of Formula II and III are reacted with the acid and promoter at a temperature of about 70° C. to about 90° C.

G. EXAMPLES

The following examples are put forth so as to provide those of ordinary skill in the art with a complete disclosure and description of how the compounds, compositions, articles, devices and/or methods claimed herein are made and evaluated, and are intended to be purely exemplary and are not intended to limit the disclosure. Efforts have been made to ensure accuracy with respect to numbers (e.g., electronic energies, binding energies, amounts, temperature, etc.), but some errors and deviations should be accounted for. Unless indicated otherwise, parts are parts by weight, temperature is in ° C. or is at ambient temperature, and pressure is at or near atmospheric. Unless indicated otherwise, percentages referring to composition are in terms of wt %.

There are numerous variations and combinations of reaction conditions, e.g., component concentrations, desired solvents, solvent mixtures, temperatures, pressures and other reaction ranges and conditions that can be used to optimize the product purity and yield obtained from the described process. Only reasonable and routine experimentation will be required to optimize such process conditions.

1. GENERAL METHODS AND MATERIALS

Unless indicated otherwise, all materials and reagents were utilized as is. All chemicals were A.R grade. As an example, 2-phenylphenol was procured from Sigma-Aldrich, Acetone from Merck, 3-Mercaptoacetic acid from Sigma-Aldrich, Concentrated HCl from SD Fine chemicals, and Concentrated $H_2SO_4$ SD Fine chemicals. Other sources can be used.

In an aspect, Proton NMR (HNMR) was used to confirm the PHP monomer. 1H NMR analysis was performed using Bruker 300 MHz instrument to perform $^1H$ Nuclear Magnetic Resonance (NMR) spectral measurements with a solution of monomer in deuterated chloroform ($CDCl_3$) or mixture of deuterated dimethylsulphoxide (DMSO-d6).

High Performance Liquid Chromatography used to assess purity of PHP monomer product. HPLC was performed using Agilent 1100 Sereis auto injector instrument having PDA detector, Water-acetonitrile as mobile phase and measured at 240 nm.

2. PREPARATION OF 2,2-BIS (3-PHENYL-4-HYDROXYPHENYL) PROPANE (PHP)

a. Example 1

In an aspect, 3 mol 2-phenylphenol, 1 mol acetone, and concentrated H2SO4 were added to a 3-necked reaction flask with nitrogen blanket equipped with condenser and overhead mechanical stirrer, followed by the addition of 600-1300 ppm (based on total reactant content) 3-Mercaptopropionic (3-mpa). The reaction mixture was heated to 80° C. for 8 hours, yielding PHP (20%).

b. Example 2

In an aspect, 3 mol 2-phenylphenol and 1 mol acetone were added to a 3-necked reaction flask with nitrogen blanket equipped with condenser and overhead mechanical stirrer, followed by the addition of 600-1300 ppm (based on total reactant content) 3-Mercaptoacetic acid (3-MPA). A purged dry HCl gas was added until saturation. The reaction mixture was heated to 80° C. for 8-10 hours, yielding PHP (50%).

c. Example 3

To a 3-necked reaction flask with nitrogen blanket equipped with condenser and overhead mechanical stirrer, 3 mol 2-phenylphenol and 1 mol acetone were added in presence of an ion exchange resin (IER) catalyst and 600-1300 ppm (based on total reactant content) of 3-Mercaptopropionic acid (3-mpa) at 80° C. for 5-14 hours, yielding PHP (10%).

d. Example 4

To a 3-necked reaction flask with nitrogen blanket equipped with condenser and overhead mechanical stirrer, 3 mol 2-phenylphenol and 1 mol acetone were added in presence of DBSA (Dodecyl benzene sulfonic acid) catalyst and 600-1300 ppm (based on total reactant content) of 3-Mercaptopropionic acid (3-mpa) at 80° C. for 12-14 hours, yielding PHP (10%).

e. Example 5

To a 3 necked reaction flask with nitrogen blanket equipped with condenser and overhead mechanical stirrer, 3 mol of 2-phenylphenol and 1 mol of acetone were added with concentrated HCl followed by the addition of 600-1300 ppm (based on total reactant content) of 3-Mercaptopropionic acid (3-mpa). The mixture was allowed to stir for 5-6 hours at 80° C. giving good conversion and good selectivity (95%) towards PHP monomer. The crude product obtained was dissolved in dichloromethane and treated with aqueous 2N sodium hydroxide for approximately 30 minutes to provide the PHP sodium salt. The precipitated PHP salt was filtered then washed with organic solvent like ethylacetate, dichloromethane to remove excess 2-phenylphenol and other impurities. The Sodium salt of PHP was dissolved in deionized water and acidified with 1N HCl to pH of 2-3, followed by 30 mins stirring. Precipitate formed was filtered and resulted in formation of more selective, more pure PHP monomer (>99%). Product was confirmed by 1H NMR and purity was confirmed by HPLC.

Utilizing a conventional in vitro competitive binding assay, estradiol binding activity can be quantified by the half maximal inhibitory concentration ($IC_{50}$) value, which can be evaluated for various monomers capable for use as component starting materials in the manufacture of polycarbonate compositions. In various aspects, these starting materials can mimic or replicate various chemical species that could be produced under certain conditions, for example high (pH=8 to 12) or low (pH=1 to 6), as hydrolysis degradation products derived from polymeric materials comprising the component starting materials.

$IC_{50}$ is defined as the concentration of the test substance at which 50% of the radioligand is displaced from the estradiol related receptor. In a further aspect, $IC_{50}$ is a quantitative measure that indicates how much of a particular substance, i.e., an inhibitor, is needed to inhibit a given biological process, by one half. $IC_{50}$ binding concentrations for the alpha in vitro estradiol receptors were tested (e.g., for 17β-estradiol control sample). Samples were dissolved in either ethanol or DMSO. Tests were conducted by displacement of a radio-ligand. Specifically, the $IC_{50}$ values described herein were determined from in-vitro experiments of the compound binding to ERR-α.

BE is the binding energy (BE) of a particular substance, more specifically a monomer, to the ERR-α receptor, and can be determined using the formula (Eqn 1.) below:

$$BE = \text{Energy(complex)} - [\text{Energy(cavity)} + \text{Energy(monomer)}]. \quad \text{(Eqn. 1)}$$

The BE calculations were performed using the Spartan software from Wavefunction Inc. as described herein. The energy is the electronic energy obtained from the density functional theory (DFT) approach described herein.

In an aspect, a 17β-estradiol control sample was evaluated to determine $IC_{50}$. In a further aspect, binding energies (B.E.) in kcal/mol of the monomers described herein were then calculated using the computational methods described herein. Such values from experimental bio-analysis are provided in Table 1.

TABLE 1

| | Compound | BE (kcal/mol) | IC50(nM) | RBA |
|---|---|---|---|---|
| A | 17β-Estradiol | −20.37 | 10.25 +/− 2.25 | 100 |
| B | 2,2-bis (3-phenyl-4-hydroxyphenyl) propane | −15.48 | | |

The PHP monomer exhibits a relatively lower binding energy (about −15.48 kcal/mol) when compared to estradiol (about −20.37 Kcal/mol) as obtained from the computational methods as described herein. In one aspect, the negative BE values indicate that the binding of monomers to the LBD cavity of ERR-α is exothermic with respect to the separated elements (i.e. cavity and ligand) as described by Eqn 1.

The patentable scope of the disclosure is defined by the claims, and can include other examples that occur to those skilled in the art. Such other examples are intended to be within the scope of the claims if they have structural elements that do not differ from the literal language of the claims, or if they include equivalent structural elements with insubstantial differences from the literal languages of the claims.

While aspects of the present disclosure can be described and claimed in a particular statutory class, such as the system statutory class, this is for convenience only and one of skill in the art will understand that each aspect of the present disclosure can be described and claimed in any statutory class. Unless otherwise expressly stated, it is in no way intended that any method or aspect set forth herein be construed as requiring that its steps be performed in a specific order. Accordingly, where a method claim does not specifically state in the claims or descriptions that the steps are to be limited to a specific order, it is no way intended that an order be inferred, in any respect. This holds for any possible non-express basis for interpretation, including matters of logic with respect to arrangement of steps or operational flow, plain meaning derived from grammatical organization or punctuation, or the number or type of aspects described in the specification.

What is claimed is:

1. A method for preparing an ortho aryl substituted bisphenol monomer comprising: reacting a ketone and a phenol in the presence of an acid catalyst and a 3-mercaptopropionic acid to produce an aromatic dihydroxy compound, wherein the aromatic dihydroxy compound is an ortho aryl substituted bisphenol monomer, and wherein the aromatic dihydroxy compound has a lower binding energy than the binding energy of estradiol to the ligand binding domain cavity of an estradiol related receptor comprising ERR-α.

2. The method of claim 1, wherein the lower binding energy is determined using the formula: binding energy=energy (complex)−[energy(cavity)+energy(monomer)], wherein the energy (complex) is an electronic energy of an optimized monomer structure in a constrained structure of the ligand binding domain cavity of the estradiol related receptor, the energy (cavity) is an electronic energy of the ligand binding domain cavity of the estradiol related receptor, and the energy (monomer) is an electronic energy of the monomer.

3. The method of claim 1, wherein the ortho aryl substituted bisphenol monomer is prepared using a batch or continuous process.

4. The method of claim 1, wherein the ketone is acetone.

5. The method of claim 1, wherein the phenol is 2-phenylphenol.

6. The method of claim 1, wherein the acid catalyst is concentrated hydrochloric acid.

7. The method of claim 1, wherein the phenol and ketone are provided at a molar ratio of at least about 2:1.

8. The method of claim 1, wherein the ketone and the phenol are reacted in a temperature range of from about 70° C. to about 90° C.

9. The method of claim 1, wherein the ketone and the phenol are reacted using a ratio of about 3.0 mole of phenol to about 1.0 mole of ketone.

10. The method of claim 1, wherein the selectivity of the reaction of the ketone and the phenol is 95:5.

11. The method of claim 1, wherein the conversion of the reaction of the ketone and the phenol is greater than about 50%.

12. A method for preparing an ortho aryl substituted bisphenol monomer as represented by Formula I:

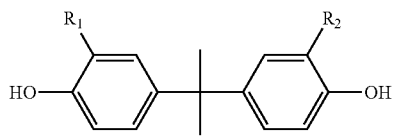

where $R_1$ and $R_2$=phenyl,
comprising:
reacting a compound represented by Formula II:

with a compound represented by Formula III:

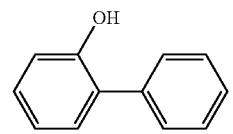 [SMILES: Oc1ccccc1-c1ccccc1]

in the presence of an acid catalyst and a promoter.

13. The method of claim 12, wherein the acid catalyst employed is concentrated hydrochloric acid and the compounds of Formula II and III are reacted with the acid and the promoter at a temperature of about 70° C. to about 90° C.

14. The method of claim 12, wherein the promoter is 3-mercaptopropionic acid and the compounds of Formula II and III are reacted with the acid and the promoter at a temperature of about 70° C. to about 90° C.

* * * * *